United States Patent [19]
McCarthy, Jr.

[11] 3,972,931
[45] Aug. 3, 1976

[54] N,N'-DISUBSTITUTED BENZAMIDINES
[75] Inventor: James R. McCarthy, Jr., Midland, Mich.
[73] Assignee: The Dow Chemical Company, Midland, Mich.
[22] Filed: Nov. 29, 1974
[21] Appl. No.: 527,989

Related U.S. Application Data
[63] Continuation-in-part of Ser. No. 456,941, April 1, 1974, abandoned, which is a continuation of Ser. No. 279,651, Aug. 10, 1972, abandoned.

[52] U.S. Cl. .................. 260/564 R; 260/501.14; 424/316; 424/326
[51] Int. Cl.² ........................................ C07C 123/00
[58] Field of Search .................. 260/564 R, 501.14

[56]  References Cited
UNITED STATES PATENTS
3,792,057  2/1974  Jensen et al. .................. 260/564 R OTHER PUBLICATIONS
Chem. Abstr., vol. 71, Col. 111,086(t) (1969).
Chem. Abstr., vol. 71, Col. 123,763(z) (1969).

Primary Examiner—Gerald A. Schwartz
Attorney, Agent, or Firm—Maynard R. Johnson

[57] ABSTRACT

N,N'-Disubstituted benzamidine compounds such as N,N'-dimethyl-3,4-dichlorobenzamidine, and their pharmaceutically-acceptable salts are prepared by the reaction of a substituted phenylacetonitrile with an alkylamine and alkylammonium salt or alternatively, by reaction of the acetonitrile or corresponding N-alkylphenylacetamide with a trialkyloxonium fluoroborate followed by reaction with a primary alkylamine. The compounds have pharmacological activity as antidepressants and antianxiety or calming agents.

6 Claims, No Drawings

N,N'DISUBSTITUTED BENZAMIDINES

CROSS-REFERENCE TO RELATED APPLICATIONS

This is a continuation-in-part of my copending application, Ser. No. 456,941, filed Apr. 1, 1974, which in turn was a continuation of my application Ser. No. 279,651, filed Aug. 10, 1972, both now abandoned.

BACKGROUND OF THE INVENTION

DESCRIPTION OF THE PRIOR ART

The substituted amidine compounds of the invention can be prepared by a modification of known methods. Typical methods which can be so modified include the reaction of a nitrile with a trialkyloxonium fluoroborate to prepare an N-alkyl nitrilium salt in a procedure similar to that of Meerwein et al., Ber. 89, 209 (1956), Borch, J. Org. Chem., 34, 627 (1969), and Weintraub et al. J. Org. Chem. 33, 1679 (1968). A number of N-monosubstituted and unsubstituted amidines are known. Craver et al. J. Pharm. Exptl. Therap. 99, 353 (1950); Netherlands Application 6,508,754, C.A. 65, 2181c (1966); U.S. Pat. Nos. 3,344,138, 3,417,122 and 3,334,137. Chlorobenzamidines are also known. Markwardt et al., Pharmazie, 1969, 24(7), 400–2, and European J. Biochem. 6; 502–6(1968).

SUMMARY OF THE INVENTION

This invention is directed to N,N'-disubstituted halobenzamidine compounds and is particularly directed to N,N'-disubstituted halobenzamidine compounds and their pharmaceutically-acceptable salts corresponding to the formula:

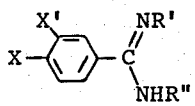

wherein X represents halo and X' represents X or hydrogen, and wherein R' and R" each independently represent loweralkyl of one to two to three carbon atoms. The compounds of the invention are generally crystalline solids at ordinary temperatures, and are variously soluble in conventional solvents such as water, alcohols, ether, benzene, chlorinated hydrocarbons and the like. The free base compounds are generally less soluble in water than the salts, particularly under alkaline conditions, while the pharmaceutically-acceptable salts are generally of moderate to good solubility in water and alcohols.

In the present specification and claims, the term "halo" is employed to designate one of the halogen moieties chloro or bromo.

The compounds of the invention are named as benzamidines. For convenience, the compounds can be referred to generically as "substituted amidines". When R' and R" are different, the amidine moiety is subject to tautomerization, e.g.

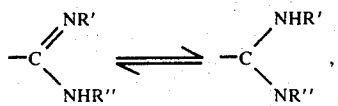

and the compound will generally be obtained as a mixture of the tautomers. Such mixtures of tautomers are useful as described herein, and for convenience will be named by naming only one tautometric form. Compounds wherein R' and R" are identical are generally preferred. The term "pharmaceutically-acceptable salt" as herein employed refers to salts of a substituted amidine which are substantially non-toxic at dosages consistant with good pharmacological activity. Such pharmaceutically-acceptable salts include nontoxic acid addition salts with inorganic acids such as hydrochloric, hydrobromic, sulfuric or phosphoric acid, or with organic acids such as acetic, succinic, malic, maleic, tartaric or citric acid, or with organic sulfonic acids such as methanesulfonic or p-toluenesulfonic acid.

The substituted amidines of the invention have been found to be useful for administration to laboratory animals in the study of drug effects on the central nervous system, and have been found to be particularly useful as antidepressants. The compounds wherein X is chloro and X' is hydrogen or chloro have excellent antidepressant activity and are preferred compounds.

The substituted amidines of the invention can be prepared by the reaction of the corresponding substituted benzonitrile with a trialkyloxonium fluoroborate to prepare the corresponding N-alkyl substituted arylnitrilium fluoroborate salt; followed by the reaction of N-alkyl substituted arylnitrilium fluoroborate with a primary alkylamine. Alternatively, the substituted amidines of the invention can be prepared by the reaction of the corresponding N-alkylbenzamide with a trialkyloxonium fluoroborate to prepare the corresponding N-alkylbenzimidate salt; followed by the reaction of N-alkylbenzimidate fluoroborate with a primary alkylamine.

These reactions are preferably carried out in the presence of an inert organic liquid such as methylene chloride or nitromethane.

In the preparation of the fluoroborate salt intermediates, the reaction proceeds when the acetonitrile or N-alkylacetamide starting material and the trialkyloxonium fluoroborate are contacted and mixed in the presence of an anhydrous organic liquid reaction medium. The mixing is carried out in dry reaction vessels under an inert gas blanket. The reaction proceeds at temperatures from about 0°C to about boiling under reflux, and is conveniently carried out at temperatures from about 25°C to about 50°C. The exact proportions of the reactants to be employed can be varied. However, it is convenient to employ from about 1 to about 3 molar proportions of the trialkyloxonium fluoroborate reactant for each molar proportion of nitrile or acetamide starting material. The reaction is generally complete within about 12 to about 72 hours depending on temperature employed. The intermediate salt can be separated by evaporation of the reaction medium, if desired, or it can be reacted with the primary alkylamine without separation. Preferably, the fluoroborate salt intermediate is not separated from the reaction mixture but is reacted directly with a primary alkylamine to prepare a substituted amidine product.

The reaction of the fluoroborate salt intermediate with the primary alkylamine proceeds when the reactants are contacted and mixed in the presence of an inert organic liquid reaction medium, such as nitromethane or methylene chloride. The reaction proceeds at temperatures of from about −70°C to about 30°C.

The exact proportions of the reactants to be employed can be varied, however, the reaction consumes the reactants in equimolar proportions, and use of the reactants in such proportions or with an excess of the primary alkylamine reactant is preferred. The reaction is generally complete in about one to about 18 hours. The product can be separated by evaporation under reduced pressure followed by the addition of aqueous alkali to neutralize any remaining fluoroborate, followed by extraction with an organic solvent such as ethyl acetate. Alternatively, the product can be isolated directly as the fluoroborate salt by evaporation of the reaction medium and washing with water. The product can be purified by conventional procedures such as washing, recrystallization, extraction, or treatment on ion exchange resins. The free base product can also be purified by conversion to a pharmaceutically-acceptable salt and purification in the salt form. When the product is obtained as the fluoroborate salt, it can be conveniently neutralized to obtain the free base which can be purified or converted to a pharmaceutically-acceptable salt.

The invention also provides a novel method for preparing the amidines by a one-step procedure using relatively inexpensive reactants, which can produce the product in a desirable form in good yields and without requiring an inert gas to protect the reactants.

In the new procedure, the N,N'-disubstituted halobenzamidines are produced by reacting the corresponding halobenzonitrile directly with the corresponding primary amine and the corresponding primary ammonium ion,

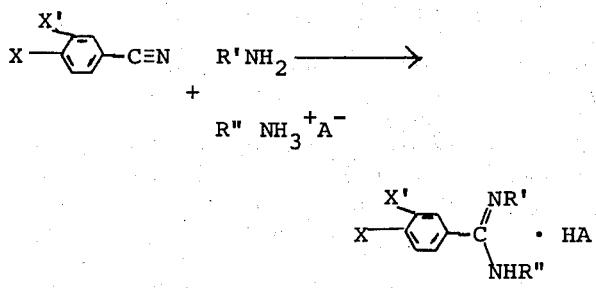

where, X, X', R' and R'' have the significance set out above, and A⁻ represents an anion. The structure of the amidine portion of the product in the above formula can also be written as

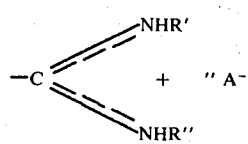

The reaction proceeds when the reactants are contacted and mixed, at a temperature in the range from about 140°C. to about 180°C. and under superatmospheric pressure. In a convenient procedure, the primary ammonium ion is conveniently supplied by using a primary ammonium salt, the anion of which (A in the above formula) is not detrimentally reactive with the other reactants. Suitable anions include inorganic anions, chloride, bromide, iodide, fluoride, sulfate, carbonate and organic anions such as toluenesulfanate, acetate, formate, etc. preferably a pharmaceutically-acceptable salt such as the chloride or bromide.

The proportions of reactants to be employed can be varied considerably; however, it is critical to employ an excess of the alkylamine. When a portion of alkylamine is employed as a salt, at least one molar proportion of the salt for each molar proportion of the nitrile starting material must be used so as to provide sufficient of the anion to obtain the product as a salt. In general, good results can be obtained by using, for each molar proportion of the nitrile, from about one to two to about 10 molar proportions of alkylamine salt; and from about 20 to about 40 molar proportions of alkylamine (free base). A lower alkanol and excess alkylamine can also serve as a reaction medium, and the maximum proportions to be employed are limited by factors such as convenience of separating the product from the medium and increased reaction time and energy requirements as the excess of reaction medium is increased.

In a convenient procedure, about 20 to 40 molar proportions alkylamine, one to ten molar proportions of alkylamine salt, and about 20 to 100 molar proportions of a lower alkanol of 1 to 3 carbon atoms are employed per molar proportion of the nitrile. The materials are mixed together in a sealed reactor; such as a bomb, and heated at a temperature of about 130° to 180°C under a pressure of about 15 to 30 atmospheres until the reaction is substantially complete, generally from about 12 to about 20 hours. Substantially anhydrous conditions are preferably maintained during this procedure. The product can be separated by conventional procedures such as evaporation or distillation to remove excess medium and low boiling starting materials. It can be purified by conventional procedures, such as liquid-liquid extraction, washing, recrystallization and the like, and can be conveniently converted to the free base, purified in that form then converted to a pharmaceutically-acceptable salt for further purification.

The pharmaceutically-acceptable salts of the free base substituted amidines can be prepared by dissolving the free base in a minimal amount of alcohol, or ether or chloroform and adding an alcohol solution of an acid such as hydrochloric acid, hydrobromic acid, or p-toluenesulfonic acid until precipitation of the corresponding salt is complete. The salt can further be purified by recrystallization or converted to the free base form.

The free base substituted amidine can be prepared by hydrolysis of the salt in aqueous base. The salt is mixed with a molar equivalent amount of sodium hydroxide in aqueous solution, excess aqueous sodium carbonate or the like, after which the free base can be separated by extraction with an organic solvent. The solvent can be removed by conventional methods such as evaporation or distillation. The product can be purified by conventional procedures such as washing or recrystallization.

DESCRIPTION OF THE PREFERRED EMBODIMENTS

The following examples illustrate the invention but are not to be construed as limiting the same.

EXAMPLE 1

34 Grams (0.18 mole) of triethyloxonium fluoroborate is dissolved in 300 milliliters of anhydrous methylene chloride and 18 grams (0.09 mole) of N-methyl-4-trifluoromethyl benzamide are added. (All glassware employed has been previously dried at 125°C and held in a dessicator prior to use). The addition is carried out under dry nitrogen. The resulting mixture is stirred for about 72 hours at a temperature of about 25° under dry nitrogen. The reaction mixture, containing the resulting substituted benzimidate fluoroborate intermediate, is cooled to a temperature of about −70°C in a Dry Iceacetone bath, and 15 grams of dry monomethylamine is added. The resulting mixture is allowed to warm to room temperature (about 25°C) and is held for about 18 hours at room temperature with stirring. The mixture is concentrated by evaporation under reduced pressure, and the residue is diluted with methylene chloride and hexane; whereupon a white precipitate forms. The mixture is filtered and the filtrate is concentrated by evaporation under reduced pressure. The residue is taken up in 30 milliliters cold aqueous 25 percent sodium hydroxide solution. The basic solution is extracted with 200 milliliters of ethyl acetate and the ethyl acetate extract is washed with water until a pH below 8 is obtained, then dried over anhydrous sodium sulfate. The ethyl acetate solution of the free base N,N'-dimethyl-4-trifluoromethylbenzamidine product is saturated with dry hydrogen chloride gas whereupon the product precipitates in the form of the hydrochloride salt. The mixture is cooled to about 5°C, and filtered to obtain the hydrochloride salt product as a filter cake. The N,N'-dimethyl-4-trifluoromethylbenzamidine hydrochloride product is recrystallized from a mixture of ethanol and ethyl acetate and found to melt at a temperature of 288°–290°C. The product is found by elemental analysis to have carbon, hydrogen and nitrogen contents of 47.28, 4.57 and 10.93 percent, respectively, as compared to the theoretical contents of 47.53, 4.78 and 11.09 percent, respectively, calculated for the named structure.

Using a similar procedure, the following are prepared:

N,N'-Dimethyl-4-chlorobenzamidine hydrochloride, melting at 285°–286°C. (recrystallized from isopropanol);

N,N'-Diisopropyl-3,4-dibromobenzamidine hydrochloride, having a molecular weight of 342.5;

N,N'-Dimethyl-3,4-dichlorobenzamidine hydrochloride, melting at 320°–321°C. (recrystallized from isopropanol);

N,N'-Di-n-propyl-4-chlorobenzamidine (free base) melting at 97°–98°C. (recrystallized from hexane);

N-Methyl-N'-ethyl-4-bromobenzamidine hydrochloride, tautomeric with N-ethyl-N'methyl-4-bromobenzamidine hydrochloride, having a molecular weight of 277.5; is prepared by using equal parts of methylamine and ethylamine; in the procedure of Example 1. The assymetrically substituted amidines are subject to tautomerism, and the product can be generally regarded as a mixture of the tautomeric forms.

The substituted amidines of the invention have pharmacological activity in alleviating central nervous system depression and in alleviating symptoms of anxiety or nervous agitation. Thus, they can be administered to mammals by conventional routes such as orally or by intraperitoneal, intramuscular or intravenous injection to alleviate central nervous system depression or anxiety symptoms. A particular advantage of the compounds is that they exhibit little or no effect on the cardiovascular system other than antithrombitic activity at dosages consistent with good central nervous system activity. The compounds can be formulated with conventional pharmaceutical excipients to facilitate administration. As with most known pharmacologically active compounds, the substituted amidines vary somewhat in activity, and the amount of compound to be employed in a given situation will depend on such factors as the exact compound or pharmaceutically-acceptable salt employed, the route of administration, the animal treated, the formulation employed, etc.

In representative operations, the compound N,N'-dimethyl-3,4-dichlorobenzamidine hydrochloride is found to protect mice against central nervous system depression and ptosis resulting from intraperitoneal injection of reserpine at a dosage rate of 2.5 milligrams reserpine, per kilogram of body weight. The test compound is found to have an intraperitoneal $ED_{50}$ of 9.3 milligrams per kilogram (mg/kg). Its intraperitoneal acute $LD_{50}$ is found to be 60 mg/kg and its oral acute $LD_{50}$ is found to be 200 mg/kg. When administered orally, the $ED_{50}$ is found to be 10.8 mg/kg for the same compound in the same procedure with mice, and 9.1 mg/kg in a similar procedure with rats. The compound is also found to potentiate hyperactivity, fighting and death resulting from subcutaneous administration of 20 mg/kg of yohimbine hydrochloride to mice aggregated in small cages. In these operations, the test compound is administered by intraperitoneal injection 30 minutes before the yohimbine challenge, and is found to potentiate lethality with an $ED_{50}$ of 2.4 mg/kg, indicating potent antidepressant action. In similar operations N,N'-dimethyl-4-chlorobenzamidine hydrochloride is found to antagonize reserpine induced ptosis in mice with an oral $ED_{50}$ of 6.2 mg/kg, and an oral $ED_{50}$ of 200 mg/kg. The test compound N,N'-dipropyl-3,4-dibromobenzamidine is found to inhibit reserpine induced ptosis when administered intraperitoneally at 30 mg/kg.

In other operations, the test compound N,N'-dimethyl-4-chlorobenzamidine hydrochloride is tested to evaluate its effect on behavior of mice trained to avoid a mild electric shock administered through the cage floor by jumping to an insulated platform. Intraperitoneal administration of 4, 10, and 21.5 mg/kg of the test compound is found to have no significant effect on the learned shock-avoidance behavior.

What is claimed is:

1. A substituted amidine compound selected from the group consisting of halobenzamidine compounds corresponding to the formula

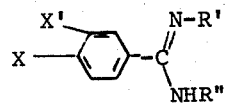

wherein X independently represents chloro or bromo and X' represents X or hydrogen, and R' and R'' each independently represent loweralkyl of one to three carbon atoms; and the pharmaceutically-acceptable salts thereof.

2. A compound of claim 1 wherein R' and R'' represent methyl.

3. A compound of claim 2 wherein X represents chloro.

4. A compound of claim 3 wherein X' represents chloro.

5. A compound of claim 1 wherein the compound is N,N'-dimethyl-4-chlorobenzamidine hydrochloride.

6. A compound of claim 1 wherein the compound is N,N'-dimethyl-3,4-dichlorobenzamidine hydrochloride.

* * * * *